(12) United States Patent
Matsushita

(10) Patent No.: US 10,206,848 B2
(45) Date of Patent: Feb. 19, 2019

(54) BEAUTY INSTRUMENT

(75) Inventor: Tsuyoshi Matsushita, Nagoya (JP)

(73) Assignee: MTG Co., ltd., Nagoya-Shi, Aichi-Ken (JP)

( * ) Notice: Subject to any disclaimer, the term of this patent is extended or adjusted under 35 U.S.C. 154(b) by 412 days.

(21) Appl. No.: 14/358,019

(22) PCT Filed: Aug. 28, 2012

(86) PCT No.: PCT/JP2012/071667
§ 371 (c)(1),
(2), (4) Date: May 13, 2014

(87) PCT Pub. No.: WO2013/073252
PCT Pub. Date: May 23, 2013

(65) Prior Publication Data
US 2014/0288473 A1  Sep. 25, 2014

(30) Foreign Application Priority Data
Nov. 16, 2011  (JP) ................. 2011-250916

(51) Int. Cl.
*A61H 15/00*  (2006.01)
*A61H 7/00*   (2006.01)
(Continued)

(52) U.S. Cl.
CPC ............ *A61H 15/00* (2013.01); *A61H 7/007* (2013.01); *A61H 15/0085* (2013.01); *A61H 15/0092* (2013.01); *A61H 39/002* (2013.01); *A61N 1/26* (2013.01); *A61H 2015/0014* (2013.01); *A61H 2015/0042* (2013.01); *A61H 2201/0165* (2013.01); *A61H 2201/10* (2013.01);
(Continued)

(58) Field of Classification Search
CPC ............ A61H 15/00; A61H 2015/0007; A61H 2015/0042; A61H 2015/0064; A61H 15/0092
USPC ................. D24/200, 211, 214, 215
See application file for complete search history.

(56) References Cited

U.S. PATENT DOCUMENTS 19,696 A   3/1858  Gage
687,363 A * 11/1901 Wirt ....................... A61H 7/003
                                                      15/188

(Continued)

FOREIGN PATENT DOCUMENTS

CN   1454582 A   11/2003
CN   2699868 Y    5/2005
(Continued)

OTHER PUBLICATIONS

MOCAP. "Hex Caps." MOCAP Plastic Vinyl Hex Caps—Product Protection, Quality Finishing. N.p., Sep. 23, 2010. Web. Jun. 16, 2017. <http://www.mocap.com/hex-vinyl-caps.html>.*
(Continued)

*Primary Examiner* — Justine Yu
*Assistant Examiner* — Christopher Miller
(74) *Attorney, Agent, or Firm* — James R. Gourley; Carstens & Cahoon, LLP

(57) ABSTRACT

A beauty instrument capable of imparting a massaging effect to skin. A beauty instrument is configured such that a pair of balls is supported at the tip of a handle. The balls are positioned at a distance from each another, and are capable of rotating around respective axes thereof.

14 Claims, 5 Drawing Sheets

(51) Int. Cl.
*A61N 1/26* (2006.01)
*A61H 39/00* (2006.01)
*A61N 1/04* (2006.01)
*A61N 1/20* (2006.01)
*A61N 1/32* (2006.01)

(52) U.S. Cl.
CPC ............ *A61H 2201/1215* (2013.01); *A61H 2201/1253* (2013.01); *A61H 2201/1671* (2013.01); *A61H 2205/022* (2013.01); *A61H 2205/04* (2013.01); *A61H 2205/06* (2013.01); *A61H 2205/10* (2013.01); *A61N 1/0408* (2013.01); *A61N 1/0472* (2013.01); *A61N 1/205* (2013.01); *A61N 1/322* (2013.01); *A61N 1/328* (2013.01)

(56) References Cited

U.S. PATENT DOCUMENTS

| | | | | |
|---|---|---|---|---|
| 1,908,051 | A * | 5/1933 | Reichl | A61H 15/0092 601/119 |
| 1,999,939 | A * | 4/1935 | Luzzi | A61H 15/0092 601/125 |
| 2,011,471 | A * | 8/1935 | Casagrande | A61H 15/0092 601/128 |
| 2,074,735 | A * | 3/1937 | Puttcamp | A61H 15/0092 15/104.001 |
| 2,621,652 | A * | 12/1952 | Ehrhardt | A61H 15/0092 492/36 |
| 2,624,335 | A * | 1/1953 | Miller | A61H 23/0263 601/125 |
| 2,688,960 | A * | 9/1954 | Fischer | A61H 23/0263 16/35 D |
| 2,691,978 | A * | 10/1954 | Kirby | A61H 15/0092 601/129 |
| 3,077,878 | A * | 2/1963 | Baulard-Cogan | A61H 15/0085 601/113 |
| 3,583,394 | A * | 6/1971 | Napoli | A61H 23/0263 482/49 |
| 3,672,355 | A * | 6/1972 | Ogawa | A61H 23/0263 601/135 |
| 3,713,186 | A * | 1/1973 | Cartwright | B60B 33/0028 16/45 |
| 3,994,289 | A * | 11/1976 | Thomas | A61H 39/04 601/120 |
| 4,149,530 | A * | 4/1979 | Gow | A61H 23/0263 601/72 |
| D272,090 | S * | 1/1984 | Hosid | D24/211 |
| 4,432,355 | A * | 2/1984 | Delluc | A46B 13/06 15/29 |
| 4,492,223 | A * | 1/1985 | Burke | A61H 15/02 401/190 |
| 5,218,955 | A * | 6/1993 | Gueret | A61H 15/0092 601/123 |
| D398,401 | S * | 9/1998 | Antoskow | D24/211 |
| 6,245,031 | B1 * | 6/2001 | Pearson | A61H 15/0092 601/118 |
| 6,299,585 | B1 * | 10/2001 | Yoo | A61H 7/001 601/118 |
| D469,879 | S * | 2/2003 | Chen | D24/211 |
| 6,726,640 | B2 * | 4/2004 | Ching-Chen | A61H 15/0092 601/107 |
| 7,481,783 | B1 * | 1/2009 | Kelley | A61H 15/0092 601/128 |
| 7,806,612 | B1 * | 10/2010 | Wangler | A46B 9/005 15/230.11 |
| D666,304 | S * | 8/2012 | Matsushita | D24/215 |
| 2003/0204153 | A1 | 10/2003 | Chen | |
| 2005/0020948 | A1 * | 1/2005 | Gueret | A45D 34/041 601/122 |
| 2006/0116614 | A1 * | 6/2006 | Jones | A61H 15/0085 601/80 |
| 2006/0155225 | A1 * | 7/2006 | Murdock | A61H 15/0092 601/131 |
| 2006/0276732 | A1 | 12/2006 | Chen | |
| 2007/0083135 | A1 | 4/2007 | Gueret | |
| 2007/0135741 | A1 * | 6/2007 | Gueret | A61H 15/0092 601/119 |
| 2008/0255484 | A1 * | 10/2008 | Gueret | A45D 34/041 601/129 |
| 2010/0049106 | A1 * | 2/2010 | Gueret | A45D 34/041 601/112 |
| 2013/0245509 | A1 * | 9/2013 | Tanigawa | A61H 15/0092 601/20 |
| 2014/0288473 | A1 | 9/2014 | Matsushita | |

FOREIGN PATENT DOCUMENTS

| | | |
|---|---|---|
| CN | 202568784 U | 12/2012 |
| JP | S63-68336 U | 5/1988 |
| JP | H03-116836 U | 12/1991 |
| JP | 04-231957 B2 | 8/1992 |
| JP | H6-36635 U | 5/1994 |
| JP | H8-159 U | 2/1996 |
| JP | 08-141031 B2 | 6/1996 |
| JP | H11-76348 A | 3/1999 |
| JP | 2000-024065 A | 1/2000 |
| JP | 2004-242770 A | 9/2004 |
| JP | 2005-095235 A | 4/2005 |
| JP | U3123693 | 7/2006 |
| JP | U3130848 | 4/2007 |
| JP | U3141605 | 5/2008 |
| JP | 2009-142509 A | 7/2009 |
| JP | U3154738 | 10/2009 |
| JP | 1374521 S | 11/2009 |
| JP | 1374522 S | 11/2009 |
| JP | U3159255 | 5/2010 |
| JP | U3164829 | 12/2010 |
| JP | U3166202 | 2/2011 |
| JP | U3166299 | 2/2011 |
| JP | 2011-120893 A | 6/2011 |
| JP | 1424182 S | 10/2011 |
| JP | 4916580 B1 | 4/2012 |
| JP | 2012-105701 A | 6/2012 |
| JP | 2012-161517 A | 8/2012 |
| JP | 2012-161517 B1 | 8/2012 |
| JP | 2015-016386 B | 1/2013 |
| JP | 2013-176681 B | 9/2013 |
| KR | 0408623 | 6/2006 |
| WO | 2010/070619 A1 | 6/2010 |
| WO | 2011/004627 A1 | 1/2011 |

OTHER PUBLICATIONS

Office Action dated Sep. 27, 2015 for JP Application No. 2011-250916 (11 pages).
Office Action dated Nov. 4, 2015 for CN Application No. 201210115400.8 (7 pages).
English machine translation of Office Action dated Nov. 4, 2015 for CN Application No. 201210115400.8 (7 pages).
International Preliminary Report on Patentability (Chapter I or Chapter II) dated May 30, 2014 for International Application No. PCT/JP2012/071667 (8 pages).
Machine translation (in English) of Office Action dated Jul. 14, 2017 for Chinese Patent Application No. 201210115400.8 (5 pages).
Machine translation (in English) of Office Action dated Sep. 25, 2018 for Japanese Patent Application No. 2018-130473 (2 pages).
Office Action dated Sep. 25, 2018 for Japanese Patent Application No. 2018-130473 (2 pages).

* cited by examiner

BEAUTY INSTRUMENT

FIELD OF THE INVENTION

The present invention relates to a beauty instrument that is capable of massaging the skin of the face, arms, other body parts, with massage balls installed on a handle, thereby promoting blood flow and achieving beautiful skin.

BACKGROUND OF THE INVENTION

Conventionally, this type of beauty instrument has been proposed in various forms. For example, Patent Document 1 has disclosed a skin treatment roller device. That is, the skin treatment roller device is provided with a shaft and a pair of rollers installed on one end of the shaft, and the rollers are set so that each of the rotation axes thereof forms an acute angle with respect to the centerline of the shaft in the longitudinal direction. Further, the angle formed between the rotation axes of the rollers is an obtuse angle. When the shaft of the skin treatment roller device is gripped by hand and the rollers are pressed against the skin in one direction, the skin is pulled to open pores. When the rollers are pulled in the opposite direction with the rollers being pressed, the skin is pinched between the rollers to contract the pores. Therefore, the skin treatment roller device is able to remove dirt of pores efficiently.

PRIOR ART DOCUMENT

Patent Document

Patent Document 1: Japanese Laid-Open Patent Publication No. 2009-142509

SUMMARY OF THE INVENTION

Problems that the Invention is to Solve

However, in the skin treatment roller device with a conventional configuration disclosed in Patent Document 1, the centerline of the shaft lies in the same plane as the rotation axes of the rollers (refer to FIG. 2 in Patent Document 1). Thus, when the shaft of the skin treatment roller device is gripped by hand to press the rollers against the skin, it is necessary to raise the elbow and bend the wrist so that the hand will be oriented toward the skin, and the shaft must stand upright with respect to the skin. Therefore, the skin treatment roller device not only operates poorly but also undergoes a great change in the state of actions of the rollers on the skin depending on the angle of the wrist.

Further, each roller of the skin treatment roller device is formed in the shape of an oval tube. Thus, when the roller device is pressed in one direction, the skin is pressed uniformly over a wide range, thus resulting in insufficient opening of pores. Still further, when the roller device is pulled in the opposite direction, the skin positioned between the rollers is pulled at a region equivalent to the length of the rollers and the skin is less likely to be strongly held between the rollers. As a result, pores are not sufficiently opened or contracted and dirt in the pores is not cleanly removed. In addition, since each roller is formed in the shape of an oval tube, the roller is in line contact with the skin to give a great resistance to the skin and does not move smoothly. Moreover, the roller device is likely to be restricted in the direction in which it moves. Therefore, the skin treatment roller device operates poorly.

Accordingly, it is an objective of the present invention to provide a beauty instrument that is capable of giving an excellent massaging effect to the skin, also giving prominent pressing and squeezing effects to the skin continuously and operates well.

Means for Solving the Problems

To achieve the foregoing objective and in accordance with the present invention, a beauty instrument is provided that includes a pair of balls, which are supported at a tip portion of a handle and located at a distance from each other, wherein each ball is rotational freely about an axis. The beauty instrument is characterized in that the axis of each ball is configured to tilt forward with respect to a centerline of the handle such that the axis of the ball is able to keep a certain angle with respect to the surface of the skin during reciprocating motion of the beauty instrument.

Effects of the Invention

The beauty instrument of the present invention is able to provide the following effects.

A pair of balls is supported at the tip portion of a handle to rotate freely about the axis thereof, with a distance therebetween, and the axis of each ball is configured to tilt forward with respect to the centerline of the handle. That is, the axis of each ball is able to keep a certain angle with respect to the surface of the skin during reciprocating motion of the beauty instrument. Therefore, when the handle is gripped and the balls are allowed to be in contact with the skin, it is not necessary to bend the wrist. The skin can be pressed when the beauty instrument is moved forward with the wrist kept straight. The skin can be squeezed when the beauty instrument is moved backward.

Further, since the part in contact with the skin is not configured with a tubular roller but with a spherical-shaped ball, the balls are partially in contact with the skin. Therefore, the balls are able to exert a pressing force and a squeezing force to the skin locally in a concentrated manner. The instrument allows the balls to move smoothly with respect to the skin and also high in freedom of movement in any direction.

Accordingly, the beauty instrument of the present invention is able to give an excellent massaging effect to the skin and to provide prominent pressing and squeezing effects on the skin continuously. The instrument also can be operated easily.

DETAILED DESCRIPTION OF THE INVENTION

A beauty instrument according to one embodiment of the present invention will be described with reference to FIGS. 1 to 7.

Figure 1:
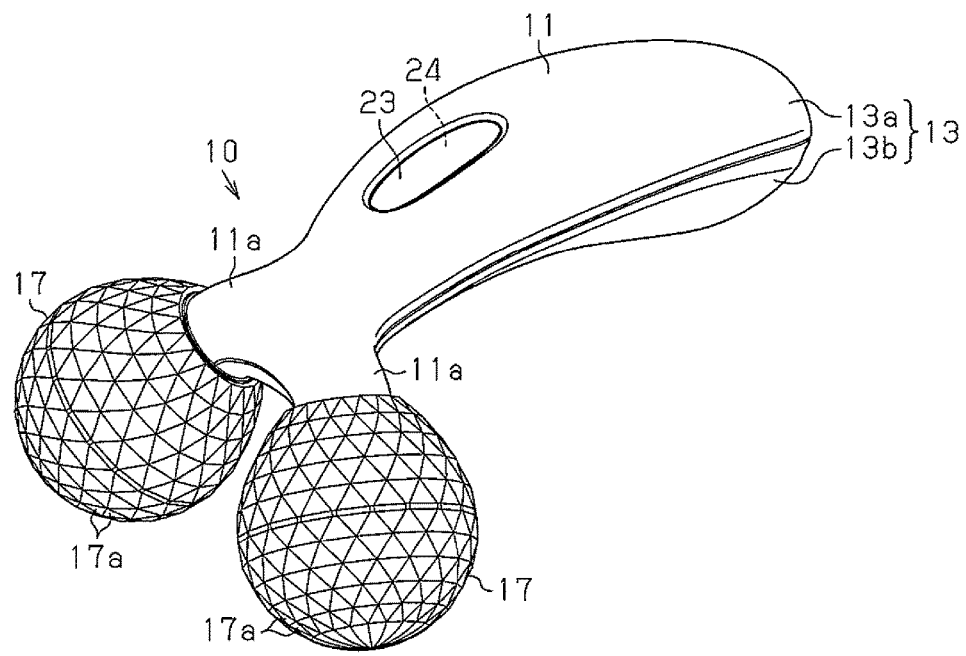
FIG. 1 is a perspective view showing a beauty instrument according to one embodiment of the present invention.
Figure 6:
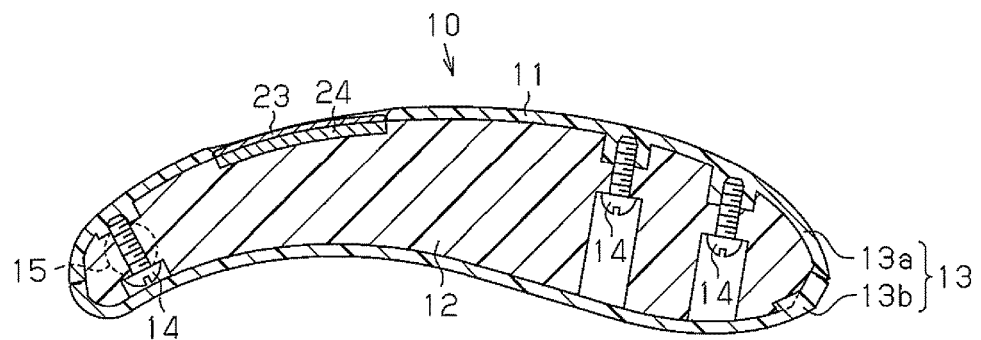
FIG. 6 is a longitudinal cross-sectional view showing the beauty instrument.

As shown in FIG. 1, a beauty instrument 10 of the present embodiment includes a handle 11, which has bifurcated portions 11a at the tip. The bifurcated portions 11a extend in a Y-letter shape in a plan view. As shown in FIG. 6, the handle 11 is configured with an electric insulating base 12, which is made of a plastic such as ABS plastic, and a handle cover 13, which is composed of an upper handle cover 13a and a lower handle cover 13b covering the outer circumference of the base 12. Each of the upper handle cover 13a and the lower handle cover 13b is made of a plastic and plated on an outer surface thereof to be electrically conductive. The handle covers 13 are coupled to the base 12 with screws 14.

Figure 7:
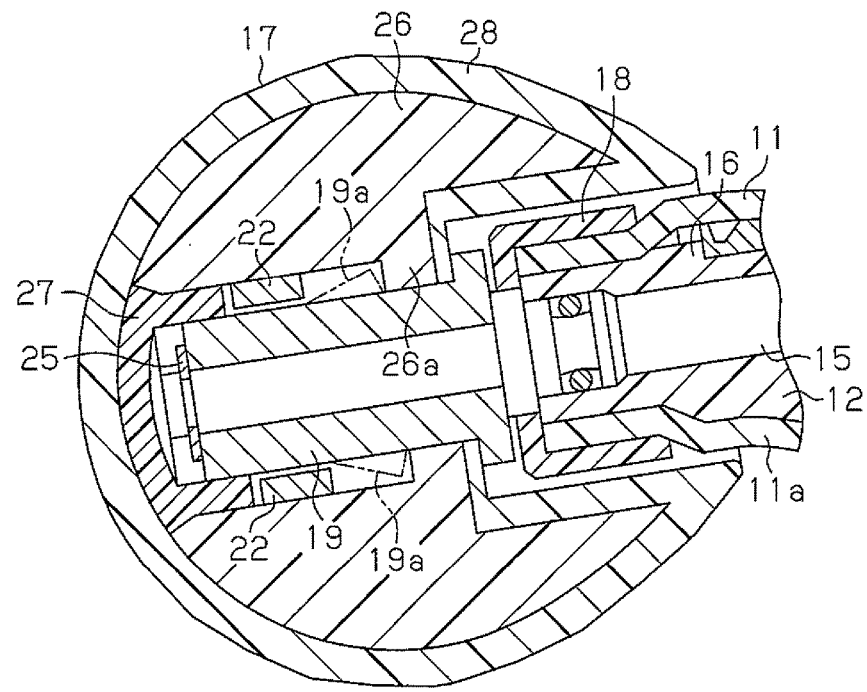
FIG. 7 is a cross-sectional view showing a rotation mechanism of the ball of the beauty instrument.

As shown in FIG. 7, a pair of supporting tubes 16 is formed integrally with the base 12 at the bifurcated portions 11a of the handle 11. A metal ball supporting shaft 15 is supported on each supporting tube 16. A cylindrical cap 18 made of a plastic is fitted and attached to the tip outer circumference of each bifurcated portion 11a of the handle 11. Due to the thus fitted and attached cap 18, the tip of the bifurcated portion 11a is sealed, the ball supporting shaft 15 is prevented from loosening. Also, electric insulation is ensured between electrically conductive portions, that is, between the outer surface of the bifurcated portion 11a and the outer surface of a ball 17, which will be described below.

A cylindrical bearing member 19, which is made of a plastic and metal-plated on the inner circumference and the outer circumference thereof, is fitted to a protruding end of the ball supporting shaft 15 and fixed by a stop ring 25 so as not to be removed. A pair of elastically deformable stoppers 19a protrudes on the outer circumference of the bearing member 19. The spherical ball 17 is inserted and supported by the bearing member 19 on the ball supporting shaft 15 to rotate freely. The ball 17 is configured with a core material 26, which is made of a plastic, a cap material 27, which is made of a plastic and fitted and attached on a tip inner circumference of the core material 26, and a shell material 28, which is made of a plastic and formed to cover the outer circumference of the core material 26.

Figure 3:
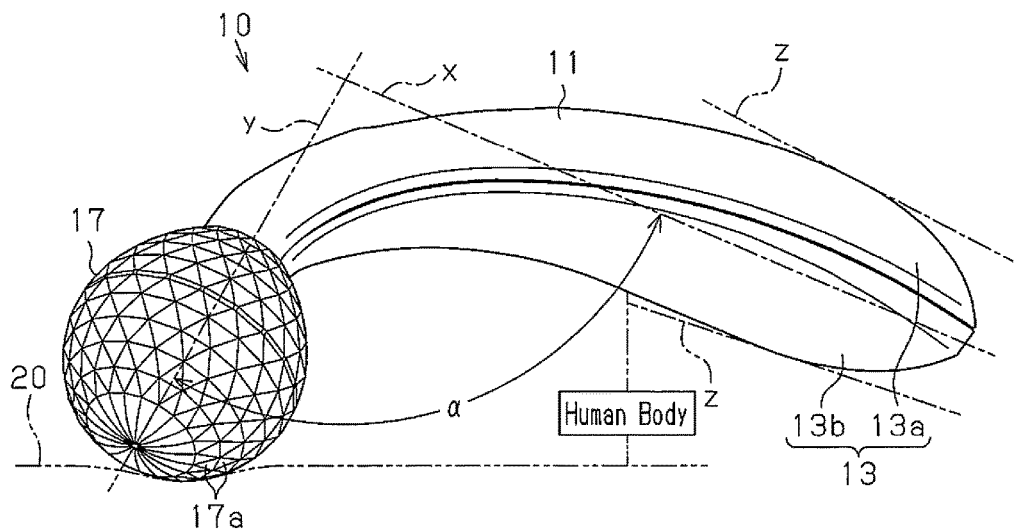
FIG. 3 is a front view showing a use condition of the beauty instrument.
Figure 4:
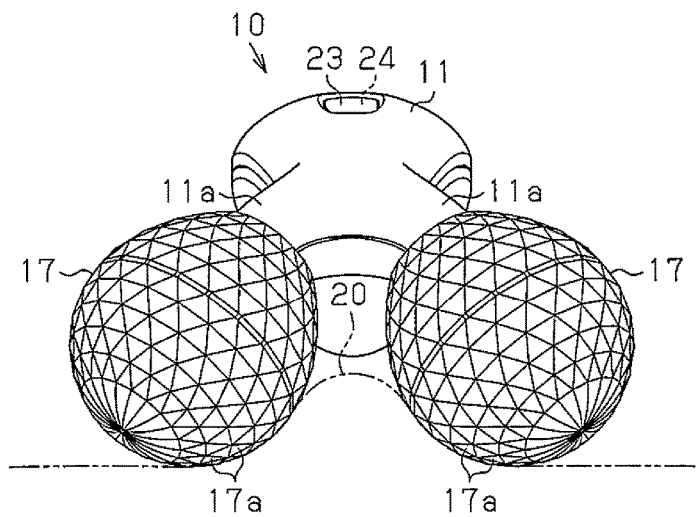
FIG. 4 is a left side view showing the beauty instrument.

The outer surface of the shell material 28 is metal-plated to be electrically conductive as an electrically conductive portion and electrically connected to the metal-plated bearing member 19. A step portion 26a is formed on an inner circumference of the core material 26. The step portion 26a can be engaged with the stoppers 19a of the bearing member 19. Then, the stoppers 19a are engaged with the step portion 26a in a state in which the ball 17 is fitted about the bearing member 19, and the ball 17 is kept so as not to be removed from the bearing member 19. Further, as shown in FIGS. 3 and 4, many faces 17a, which stimulate tissues of the skin 20, are formed on the outer circumferential surface of each of the balls 17.

A permanent magnet 22 for generating electric power in association with rotation of the ball 17 is located inside each of the balls 17 a. The permanent magnet 22 is made of magnetic steel in a cylindrical shape and configured to rotate in an integral manner with the ball 17. As the ball 17 rotates, the permanent magnet 22 rotates relative to the ball supporting shaft 15 with a slight distance in between. Thereby, a micro electric power is generated due to very small irregularities on the surface of the ball supporting shaft 15 and slight deviation of roundness, and the micro electric power is transmitted to the electrically conductive portion of the outer circumferential surface of the ball 17.

Figure 2:
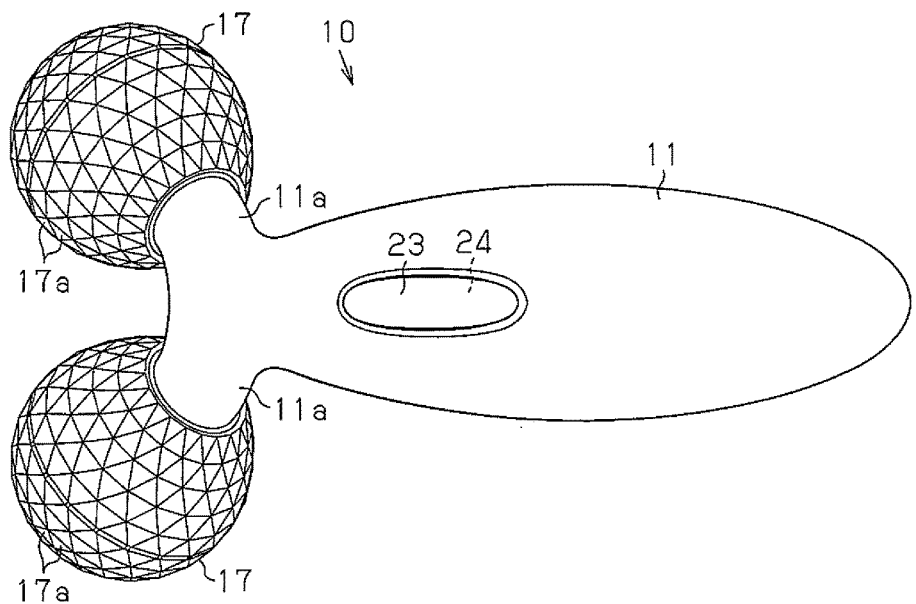
FIG. 2 is a plan view showing the beauty instrument.

As shown in FIGS. 2 and 6, a transparent plate 23 is installed on the tip of the handle 11, in other words, at the root of the bifurcated portions 11a. A solar cell panel 24 is installed inside the transparent plate 23. An output terminal (not illustrated) of the solar cell panel 24 is connected to electrically conductive portions of the handle 11 and the balls 17. Therefore, electricity generated at the solar cell panel 24 is supplied to the electrically conductive portions of the handle 11 and the balls 17. As a result, when the beauty instrument 10 is used, electricity generated at the solar cell panel 24 between the handle 11 and the balls 17 runs through the human body, thereby making it possible to provide cosmetic effects.

As described previously, the beauty instrument 10 of the present embodiment can be applied to the face and also can be applied to other parts of the body such as the neck, arms and legs.

As shown in FIG. 3, the axis of the ball supporting shaft 15 is configured to tilt forward with respect to the centerline x of the handle 11 such that the axis of the ball supporting shaft 15 can keep a certain angle with respect to the surface of the skin 20 while the beauty instrument 10 is in reciprocating motion. More specifically, a lateral projection angle α of an axis y of the ball 17, that is, an axis y of the ball supporting shaft 15 with respect to the centerline x (a line parallel with a line that divides an angle between outer circumferential tangent lines z of the thickest part of the handle 11) of the handle 11 is preferably from 90 degrees to 110 degrees in order that the ball 17 tilts forward with respect to the centerline x of the handle 11 to improve operability. It is more preferable that the lateral projection angle α is from 93 degrees to 100 degrees. It is most preferable that the angle is from 95 degrees to 99 degrees. If the lateral projection angle α is less than 90 degrees and if it is greater than 110 degrees, the ball supporting shaft 15 tilts forward to an excessively lesser or greater extent. Thus, when the balls 17 are in contact with the skin 20, it is necessary to raise or lower the elbow or widely bend the wrist. As a result, the beauty instrument 10 is poor in operability and also it is difficult to adjust the angle of the ball supporting shaft 15 with respect to the surface of the skin 20.

Figure 5:
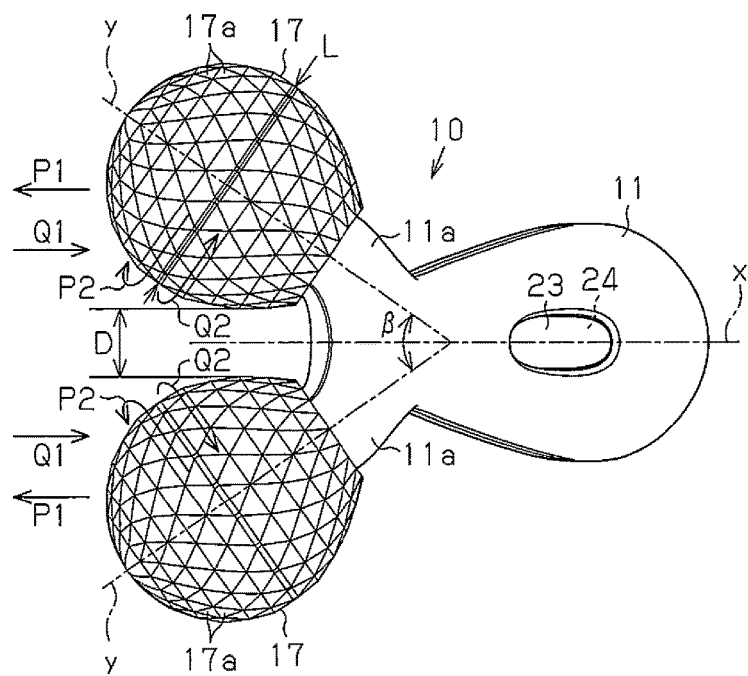
FIG. 5 is a plan view showing a state in which a plane including axes of the balls of the beauty instrument is horizontal.

As shown in FIG. 5, the opening angle between the balls 17, that is, an opening angle β between the ball supporting shafts 15 is set preferably from 50 degrees to 110 degrees, more preferably from 50 degrees to 90 degrees, and particularly preferably from 65 degrees to 80 degrees in order that reciprocating motion of the balls 17 gives a favorable pressing effect and a squeezing effect to the skin 20. If the opening angle β is less than 50 degrees, there is a tendency that the squeezing effect given to the skin 20 is excessively strong and this is not favorable. On the other hand, if the opening angle β is in excess of 110 degrees, the skin 20 positioned between the balls 17 is squeezed with difficulty, and this is not favorable either.

Further, a diameter L of each of the balls 17 is preferably set from 15 mm to 60 mm, more preferably from 32 mm to 55 mm, and particularly preferably from 38 mm to 45 mm in order that the beauty instrument 10 is applied mainly to the face and arms. If the diameter L of the ball 17 is smaller than 15 mm, the pressing effect and the squeezing effect are provided at a smaller range of the skin 20, and this is not favorable. On the other hand, if the diameter L of the ball 17 is greater than 60 mm, the ball 17 is dimensionally large in relation to the face and arms. Thus, it is difficult for the instrument to press or squeeze a narrow part and is poor in usability.

Still further, a distance D between the outer circumferential surfaces of the balls 17 is preferably from 8 mm to 25 mm, more preferably from 9 mm to 15 mm, and particularly preferably from 10 mm to 13 mm in order that the skin 20 is squeezed in an appropriate manner in particular. If the distance D between the outer circumferential surfaces of the balls 17 is less than 8 mm, the squeezing effect is given too strongly to the skin 20 positioned between the balls 17 and this is not favorable. On the other hand, if the distance D between the outer circumferential surfaces of the balls 17 is in excess of 25 mm, it is difficult to squeeze the skin 20 positioned between the balls 17, and this is not favorable either.

Next, operation of the beauty instrument 10 of the embodiment which is configured as described above will be described.

When the beauty instrument 10 is used, as shown in FIG. 3, a user presses the outer circumferential surfaces of the balls 17, while gripping the handle 11, and causes the balls 17 to contact the skin 20 such as the face and arms as shown in an alternate long and two short dashed line shown in FIG. 3, and moves the instrument forward in a direction moving from the base end of the handle 11 to the tip thereof (the leftward direction in FIG. 3). Then, the balls 17 are rotated about the ball supporting shafts 15. At this time, as shown in the alternate long and two short dashed line in FIG. 3, a pressing force is applied to the skin 20 from the balls 17. When the instrument is moved backward so that the balls 17 are returned to original positions after forward movement of the balls 17, the skin 20 positioned between the balls 17 is squeezed in association with rotation of the balls 17 as shown in the alternate long and two short dashed line in FIG. 4.

That is, as shown in FIG. 5, when the balls 17 are moved forward in a direction of arrows P1, each of the balls 17 is rotated in a direction of arrows P2. Therefore, the skin 20 is pressed and stretched. On the other hand, when the balls 17 are moved backward in a direction of arrows Q1, each of the balls 17 is rotated in a direction of arrows Q2. Therefore, the skin 20 positioned between the balls 17 is squeezed to be wound up. The balls 17 press the skin 20 during forward movement, by which the skin 20 between the balls 17 is squeezed as a reaction of the pressing force thereof.

In this case, the ball supporting shafts 15 tilt forward with respect to the centerline x of the handle 11. More specifically, the lateral projection angle α of the ball supporting shafts 15 with respect to the centerline x of the handle 11 is set from 90 degrees to 110 degrees. Thus, it is possible to reciprocate the beauty instrument 10 without raising the elbow or bending the wrist too much. Further, the beauty instrument can be operated continuously such that the axes y of the ball supporting shafts 15 are kept substantially at a right angle with respect to the surface of the skin 20. As a result, the balls 17 are efficiently pressed against the skin 20, thus making it possible to provide an efficient massage effect.

Still further, a part in contact with the skin 20 is configured not with conventional tubular rollers but with the spherical balls 17. The balls 17 are in contact with the skin 20 at an area smaller than that of the rollers. Therefore, the balls 17 are able to exert a pressing force and a squeezing force to the skin 20 locally in a concentrated manner.

Further, the balls 17 are able to move smoothly with respect to the skin 20 and also to change a moving direction easily.

Therefore, due to a pressing force in association with rotation of the balls 17, the skin 20 such as the face and arms is massaged to promote blood flow at the massaged part and also promote circulation of lymphatic fluid. Further, the opening angle β between the balls 17 is set from 50 degrees to 110 degrees and the distance D between the outer circumferential surfaces of the balls 17 is set from 8 mm to 25 mm. It is, therefore, possible to apply an appropriate pressing force to a desired site of the skin 20 and also to squeeze the skin 20 not excessively strong or not excessively weak, in a comfortable manner. Still further, the diameter L of the ball 17 is set from 15 mm to 60 mm. Thus, the beauty instrument 10 is able to massage the face and arms in an appropriate manner and also operated quickly. Therefore, a lift massage can be given, for example, to a loosened part of the skin 20, as desired.

In addition, when the skin 20 is pulled by a pressing force of the balls 17, pores are opened, and when the skin 20 is squeezed between the balls 17, the pores are contracted to remove dirt inside the pores. Further, the skin 20 of the user is in contact with the outer circumferential surfaces of the balls 17 and the hand of the user is also in contact with an electrically conductive portion on the surface of the handle 11. Therefore, due to electricity generated by the solar cell panel 24, as shown in FIG. 3, weak electric current flows from the balls 17 to the skin 20 via the hand of the user, thereby stimulating the skin 20 to promote blood flow and circulation of lymphatic fluid. Thus, the massaging actions, pressing/squeezing actions, lift-up actions, actions of removal of dirt inside pores, electrically stimulating actions are applied to the skin 20 in a synergistic and comprehensive manner, thereby giving desirable skin treatment effects to the skin.

Therefore, according to the present embodiment, the following advantages are obtained.

(1) In the beauty instrument 10 of the present embodiment, the balls 17 are arranged at a distance and supported to rotate about the axis y. The lateral projection angle α of the axis y of each ball 17 with respect to the centerline x of the handle 11 is set from 90 degrees to 110 degrees such that the ball supporting shaft 15 tilts forward with respect to the centerline x of the handle 11. That is, since the axis y of the ball 17 tilts forward with respect to the centerline x of the handle 11, it is not necessary to raise the elbow or bend the wrist greatly, when bringing the balls 17 into contact with the skin 20 while gripping the handle 11. As a result, the user is able to press and squeeze the skin 20 by easily reciprocating the beauty instrument 10.

Further, the part in contact with the skin 20 is configured with the spherical-shaped balls 17. It is, thus, possible to apply the pressing force and the squeezing force to a desired part of the skin 20 in a concentrated manner. The balls 17 are also allowed to move smoothly with respect to the skin 20 and also high in freedom of movement in any direction.

Therefore, according to the beauty instrument 10 of the present embodiment, that not only is an excellent massaging effect given to the skin 20 but also prominent pressing and squeezing effects are given to the skin 20 continuously and the instrument is excellent in operability.

(2) The lateral projection angle α of the axis y of the ball 17 is preferably from 93 degrees to 100 degrees and more preferably from 95 degrees to 99 degrees. Therefore, it is possible to improve operability of the beauty instrument 10 and cosmetic effects such as massaging effect to a greater extent.

(3) The opening angle β between the balls 17 is preferably from 50 degrees to 110 degrees, more preferably from 50 degrees to 90 degrees, and particularly preferably from 65 degrees to 80 degrees. Therefore, it is possible to improve a pressing effect and a squeezing effect of the beauty instrument 10 drastically.

(4) The diameter L of the ball 17 is preferably from 15 mm to 60 mm, more preferably from 32 mm to 55 mm, and particularly preferably from 38 mm to 45 mm. Therefore, the beauty instrument 10 can be applied favorably to the face and arms. It is possible to improve the massaging effect and operability of the instrument.

(5) The distance D between the outer circumferential surfaces of the balls 17 is preferably from 8 mm to 25 mm, more preferably from 9 mm to 15 mm, and particularly preferably from 10 mm to 13 mm. Therefore, it is possible to apply an appropriate pressing effect to a desired site of the skin 20. Also the skin 20 can be squeezed comfortably with an appropriate strength.

(6) In the beauty instrument 10, the power source is composed of the solar cell panel 24 installed on the handle 11. Therefore, it is not necessary to install a power source such as a dry cell. Weak electric current is allowed to flow from the balls 17 to the skin 20 by using electricity generated at the solar cell panel 24.

(7) The permanent magnet 22 for generating electricity in association with rotation of the balls 17 is provided in the beauty instrument 10 of the present embodiment. Thus, micro electric power can be obtained by rotation of the balls 17 and the micro electric power thereof is able to impart weak electric current from the balls 17 to the skin 20.

EXAMPLES

Hereinafter, a more specific description will be given of the previously described embodiment with reference to examples.

Examples 1 to 6, Evaluation of Lateral Projection Angle α

In the beauty instrument 10 of the previously described embodiment, which is applicable to both the face and the body, the lateral projection angle α was evaluated while changing the angle α from 90 degrees to 110 degrees under the condition where the opening angle β between the balls 17 was set to be 70 degrees, the diameter L of the ball 17 was set to be 40 mm, and the distance D between the outer circumferential surfaces of the balls 17 was set to be 11 mm. That is, the beauty instrument 10 was applied to body parts such as the face, arms and neck, thereby carrying out a sensory evaluation for feeling during use.

The sensory evaluation was conducted using the following procedures. That is, ten persons evaluated the feeling during use of the beauty instrument 10. When eight or more of them evaluated the feeling during use to be good, "A" was given, when five to seven of them evaluated the feeling during use to be good, "B" was given, when three or four of them evaluated the feeling during use to be good, "C" was given, and when two or less of them evaluated the feeling during use to be good, "D" was given.

Table 1 shows the results.

TABLE 1

| | Lateral projection angle: α (degrees) | Evaluation |
|---|---|---|
| Example 1 | 90 | C |
| Example 2 | 93 | B |
| Example 3 | 97 | A |
| Example 4 | 99 | A |
| Example 5 | 100 | B |
| Example 6 | 110 | C |

As shown in Table 1, the best results were obtained in Example 3, where the lateral projection angle α was 97 degrees, and in Example 4, where it was 99 degrees. Then, better results were obtained in Example 2, where the lateral projection angle α was 93 degrees, and in Example 5, where it was 100 degrees. Further, results of Example 1, where the lateral projection angle α was 90 degrees, and those of Example 6, where it was 110 degrees, were also judged to be acceptable.

Therefore, the lateral projection angle α of the beauty instrument 10 was preferably in a range from 90 degrees to 110 degrees and more preferably in a range from 93 degrees to 100 degrees.

Examples 7 to 15, Evaluation of Opening Angle β

Evaluation was conducted for the opening angle β of a beauty instrument 10 that was suitable for both the face and the body. That is, the opening angle β was evaluated while changing the opening angle β from 40 degrees to 120 degrees under the condition where the lateral projection angle α of the beauty instrument 10 was set to be 97 degrees, the diameter L of the ball 17 was set to be 40 mm, and the distance D between the outer circumferential surfaces of the balls 17 was set to be 11 mm. The evaluation was conducted in the same way as that of the previously described Example 1. Table 2 shows the thus obtained results.

TABLE 2

| | Opening angle: β (degrees) | Evaluation |
|---|---|---|
| Example 7 | 40 | C |
| Example 8 | 50 | B |
| Example 9 | 55 | B |
| Example 10 | 60 | B |
| Example 11 | 70 | A |
| Example 12 | 90 | B |
| Example 13 | 100 | B |
| Example 14 | 110 | B |
| Example 15 | 120 | C |

As shown in Table 2, the best result was obtained in Example 11, where the opening angle β was 70 degrees. Then, better results were obtained in Example 8 to Example 10, where the opening angle β was 50 degrees to 60 degrees and in Example 12 to Example 14, where it was 90 degrees to 110 degrees. Further, results of Example 7, where the opening angle β was 40 degrees and those of Example 15, where it was 120 degrees were also judged to be acceptable.

Therefore, the opening angle β of the beauty instrument 10 was judged to be preferable in a range from 50 degrees to 110 degrees and most preferable in a range from 65 degrees to 80 degrees.

Example 16 to Example 23, Evaluation of Diameter L of Ball 17

Evaluation was conducted for the diameter L of the ball 17 of a beauty instrument 10 that was suitable for both the face and the body. That is, the diameter L of the ball 17 was evaluated while changing the diameter L from 20 mm to 40 mm under conditions where the lateral projection angle α of the beauty instrument 10 was set to be 97 degrees, the opening angle β between the balls 17 was set to be 70 degrees, and the distance D between the outer circumferential surfaces of the balls 17 was set to be 11 mm. The evaluation was conducted in the same way as that of the previously described Example 1. Table 3 shows the thus obtained results.

TABLE 3

|  | Diameter of ball: L (mm) | Evaluation |
| --- | --- | --- |
| Example 16 | 20 | C |
| Example 17 | 25 | C |
| Example 18 | 27.5 | C |
| Example 19 | 30 | C |
| Example 20 | 32.5 | C |
| Example 21 | 35 | B |
| Example 22 | 38.3 | A |
| Example 23 | 40 | A |

As shown in Table 3, the best results were obtained in Example 22, where the diameter L of the ball 17 was 38.3 mm, and in Example 23, where it was 40 mm. Then, better results were obtained in Example 21, where the diameter L of the ball 17 was 35 mm. Further, results of Examples 16 to 20, where the diameter L of the ball 17 was from 20 mm to 32.5 mm were also judged to be acceptable.

Therefore, the diameter L of the ball 17 of the beauty instrument 10 was judged to be preferable in a range from 20 mm to 40 mm, more preferable in a range from 35 mm to 40 mm, and most preferable in a range from 38.3 mm to 40 mm.

Examples 24 to 28, Evaluation of the Distance D Between the Outer Circumferential Surfaces of the Balls 17

Evaluation was conducted for the distance D between the outer circumferential surfaces of the balls 17 in a beauty instrument 10 that was suitable for both the face and the body. That is, the distance D between the outer circumferential surfaces of the balls 17 was evaluated while changing the distance D from 8 mm to 15 mm under the condition where the lateral projection angle α of the beauty instrument 10 was set to be 97 degrees, the opening angle β between the balls 17 was set to be 70 degrees, and the diameter L of the ball 17 was set to be 40 mm. The evaluation was conducted in the same way as that of the previously described Example 1. Table 4 shows the thus obtained results.

TABLE 4

|  | Distance between balls: D (mm) | Evaluation |
| --- | --- | --- |
| Example 24 | 8 | C |
| Example 25 | 10 | B |
| Example 26 | 11 | A |
| Example 27 | 12 | B |
| Example 28 | 15 | C |

As shown in Table 4, the best result was obtained in Example 26, where the distance D between the outer circumferential surfaces of the balls 17 was 11 mm. Then, better results were obtained in Example 25, where the distance D between the outer circumferential surfaces of the balls 17 was 10 mm and in Example 27, where the distance D was 12 mm. Further, results of Example 24, where the distance D between the outer circumferential surfaces of the balls 17 was 8 mm and those of Example 28, where it was 15 mm were also judged to be acceptable.

Therefore, the distance D between the outer circumferential surfaces of the balls 17 of the beauty instrument 10 was judged to be preferable in a range from 8 mm to 15 mm, and more preferable in a range from 10 mm to 12 mm.

Examples 29 to 38, Evaluation of Diameter L of the Ball 17

Evaluation was conducted for the diameter L of the ball 17 in a beauty instrument 10 that was mainly suitable for the face. That is, the diameter L of the ball 17 was evaluated while changing the diameter L from 15 mm to 40 mm under the condition where the lateral projection angle α of the beauty instrument 10 was set to be 97 degrees, the opening angle β between the balls 17 was set to be 70 degrees, and the distance D between the outer circumferential surfaces of the balls 17 was set to be 11 mm. The evaluation was conducted in the same way as that of Example 1. Table 5 shows the thus obtained results.

TABLE 5

|  | Diameter of the ball: L (mm) | Evaluation |
| --- | --- | --- |
| Example 29 | 15 | B |
| Example 30 | 17 | B |
| Example 31 | 20 | B |
| Example 32 | 25 | A |
| Example 33 | 27.5 | A |
| Example 34 | 30 | B |
| Example 35 | 32.5 | C |
| Example 36 | 35 | C |
| Example 37 | 38.3 | C |
| Example 38 | 40 | C |

As shown in Table 5, in the case of the beauty instrument 10 for the face, the best results were obtained in Example 32, where the diameter L of the ball 17 was 25 mm, and in Example 33, where it was 27.5 mm. Then, better results were obtained in Examples 29 to 31, where the diameter L of the ball 17 was from 15 mm to 20 mm and in Example 34, where the diameter L of the ball 17 was 30 mm. Further, results of Examples 35 to 38, where the diameter L of the ball 17 was from 32.5 mm to 40 mm were also judged to be acceptable.

Therefore, when the beauty instrument 10 was suitable for the face, the diameter L of the ball 17 was judged to be preferable in a range from 15 mm to 40 mm and more preferable in a range from 15 mm to 30 mm.

Examples 39 to 44, Evaluation of the Distance D Between the Outer Circumferential Surfaces of Balls 17

Evaluation was conducted for the distance D between the outer circumferential surfaces of the balls 17 in a beauty instrument 10 that was mainly suitable for the face. That is, the distance D between the outer circumferential surfaces of the balls 17 was evaluated while changing the distance D from 6 mm to 15 mm under the condition where the lateral projection angle α of the beauty instrument 10 was set to be 97 degrees, the opening angle β between the balls 17 was set to be 70 degrees, and the diameter L of the ball 17 was set to be 40 mm. The evaluation was conducted in the same way as that of the previously described Example 1. Table 6 shows the thus obtained results.

TABLE 6

| | Distance between balls: D (mm) | Evaluation |
| --- | --- | --- |
| Example 39 | 6 | C |
| Example 40 | 8 | B |
| Example 41 | 10 | B |
| Example 42 | 11 | A |
| Example 43 | 12 | B |
| Example 44 | 15 | C |

As shown in Table 6, when the beauty instrument 10 was for the face, the best result was obtained in Example 42, where the distance D between the outer circumferential surfaces of the balls 17 was 11 mm. Then, better results were obtained in Example 40, where the distance D between the outer circumferential surfaces of the balls 17 was 8 mm, in Example 41, where the distance D was 10 mm and in Example 43, where it was 12 mm. Further, results of Example 39, where the distance D between the outer circumferential surfaces of the balls 17 was 6 mm and those of Example 44, where it was 15 mm were also judged to be acceptable.

Therefore, when the beauty instrument 10 was for the face, the distance D of the outer circumferential surfaces of the balls 17 was judged to be preferable in a range from 6 mm to 15 mm and more preferable in a range from 8 mm to 12 mm.

Examples 45 to 51, Evaluation of the Diameter L of the Ball 17

Evaluation was conducted for the diameter L of the ball 17 in a beauty instrument 10 that was mainly suitable for the body. That is, the diameter L of the ball 17 was evaluated while changing the diameter L from 30 mm to 60 mm under the conditions where the lateral projection angle α of the beauty instrument 10 was set to be 97 degrees, the opening angle β between the balls 17 was set to be 70 degrees, and the distance D between the outer circumferential surfaces of the balls 17 was set to be 11 mm. The evaluation was conducted in the same way as that of the previously described Example 1. Table 7 shows the thus obtained results.

TABLE 7

| | Diameter of ball: L (mm) | Evaluation |
| --- | --- | --- |
| Example 45 | 30 | C |
| Example 46 | 32.5 | C |
| Example 47 | 35 | C |
| Example 48 | 38.3 | B |
| Example 49 | 40 | B |
| Example 50 | 50 | A |
| Example 51 | 60 | A |

As shown in Table 7, the best results were obtained in Example 50, where the diameter L of the ball 17 was 50 mm, and in Example 51, where it was 60 mm. Then, better results were obtained in Example 48, where the diameter L of the ball 17 was 38.3 mm, and in Example 49, where the diameter L of the ball 17 was 40 mm. Further, results of Examples 45 to 47, where the diameter L of the ball 17 was from 30 mm to 35 mm were also judged to be acceptable.

Therefore, when the beauty instrument 10 was for the body, the diameter L of the ball 17 was judged to be preferable in a range from 30 mm to 60 mm and more preferable in a range from 38.3 mm to 60 mm.

Examples 52 to 58, Evaluation of the Distance D Between the Outer Circumferential Surfaces of the Balls 17

Evaluation was conducted for the distance D of the outer circumferential surfaces of the balls 17 in a beauty instrument 10 that was mainly suitable for the body. That is, the distance D between the outer circumferential surfaces of the balls 17 was evaluated while changing the distance D from 8 mm to 25 mm under the condition where the lateral projection angle α of the beauty instrument 10 was set to be 97 degrees, the opening angle β between the balls 17 was set to be 70 degrees, and the diameter L of the ball 17 was set to be 40 mm. The evaluation was conducted in the same way as that of the previously described Example 1. Table 8 shows the thus obtained results.

TABLE 8

| | Distance between balls: D (mm) | Evaluation |
| --- | --- | --- |
| Example 52 | 8 | C |
| Example 53 | 10 | B |
| Example 54 | 11 | B |
| Example 55 | 12 | A |
| Example 56 | 15 | A |
| Example 57 | 20 | B |
| Example 58 | 25 | B |

As shown in Table 8, the best results were obtained in Example 55, where the distance D between the outer circumferential surfaces of the balls 17 was 12 mm, and in Example 56, where it was 15 mm. Then, better results were obtained in Example 53 and Example 54, where the distance D between the outer circumferential surfaces of the balls 17 was from 10 mm to 11 mm, and in Example 57 and Example 58, where it was 20 mm to 25 mm. Further, the result of Example 52, where the distance D of the outer circumferential surfaces of the balls 17 was 8 mm, was also judged to be acceptable.

Therefore, when the beauty instrument 10 was for the body, the distance D between the outer circumferential surfaces of the balls 17 was judged to be preferable in a range from 8 mm to 25 mm and more preferable in a range from 10 mm to 25 mm.

With the comprehensive evaluation given to the results of Examples 1 to 58 so far shown, the lateral projection angle α of the beauty instrument 10 was required to be in a range from 90 degrees to 110 degrees. The lateral projection angle α was judged to be preferable in a range from 93 degrees to 100 degrees and in particular preferable in a range from 95 degrees to 99 degrees. The opening angle β between the balls 17 was judged to be preferable in a range from 50 degrees to 110 degrees, more preferable in a range from 50 degrees to 90 degrees, and in particular preferable in a range from 65 degrees to 80 degrees. The diameter L of the ball 17 was judged to be preferable in a range from 15 mm to 60 mm, more preferable in a range from 32 mm to 55 mm and in particular preferable in a range from 38 mm to 45 mm. The distance D between the outer circumferential surfaces of the balls 17 was judged to be preferable in a range from 8 mm to 25 mm, more preferable in a range from 9 mm to 15 mm and in particular preferable in a range from 10 mm to 13 mm.

The above embodiment may be modified as follows.

Figure 8:
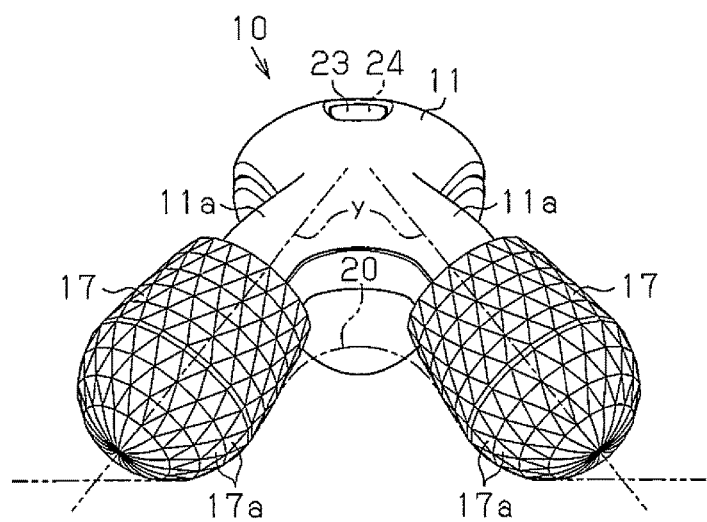
FIG. 8 is a left side view showing a beauty instrument according to a modification.
Figure 9:
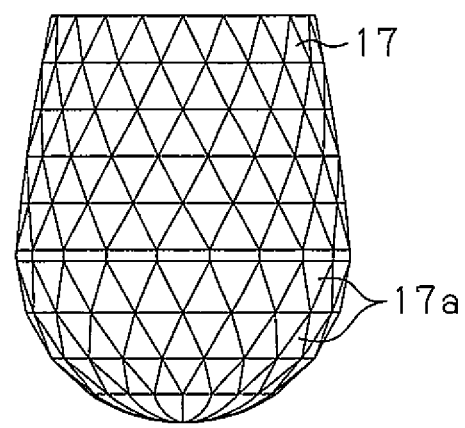
FIG. 9 is a front view showing the ball of the beauty instrument of the modification.

As shown in FIGS. 8 and 9, the shape of the ball 17 may also be formed in a balloon shape such that the curvature of the outer circumferential surface of the ball 17 on the side closer to the handle 11 is greater than the curvature thereof at the tip side of the ball supporting shaft 15. In the above configuration, the skin can be squeezed at the part of the smaller curvature and the skin can be kept squeezed at the part of the greater curvature. Therefore, the skin 20 can be squeezed more effectively when the balls 17 are moved backward.

In order to make changeable the lateral projection angle α of the axis y of the ball 17 with respect to the centerline x of the handle 11, the handle 11 and the bifurcated portions 11a may be configured to be pivoted relative to each other. In this case, the angle of the axis y of each ball 17 can be easily changed with respect to the skin 20, resulting in an improvement in usability of the beauty instrument.

The ball 17 may be changed into a shape the cross section of which is an oval or an ellipse, whenever necessary.

A magnet may be buried into the outer circumferential part of the ball 17 to promote blood flow of the skin 20 by the magnetic force thereof.

A photocatalyst such as titanium oxide may be buried into the outer circumferential part of the ball 17 to suppress adhesion of dirt on the surface of the skin or to oxidize dirt.

Alumina-based ceramic or zirconium-based ceramic, which emit far infrared rays, may be contained in the ball 17, thereby irradiating far infrared rays to the skin 20.

It is also possible to use a dry cell in place of the solar cell panel 24.

It is possible that the upper handle cover 13a or the lower handle cover 13b is not subjected to electrically conductive plating, but the upper handle cover 13a and the lower handle cover 13b are directly made of an electrically conductive plastic in which electrically conductive powder such as carbon black or metal is dispersed into a plastic.

The electrically insulating material that forms the base 12 of the handle 11 and the handle cover 13 may include plastics such as acrylic plastic and polypropylene plastic, in addition to nylon plastic and ABS plastic.

It is also possible to form the faces 17a of the ball 17 in the shape of a polygon or a circle other than a triangle. The faces 17a may also be formed into various patterns such as a vertical stripe pattern, a horizontal strip pattern, a swirling stripe pattern, a matt finish, and a pattern-free.

It is also possible to omit the permanent magnet 22 or the solar cell panel 24.

It is also possible to change the shape of the handle 11. It can be formed in the shape of a cylinder, a circular column, or a rectangular column. In this case, the lateral projection angle α is an angle with respect to the axis of the handle 11. The handle 11 can be formed in a concave-convex shape and in a gourd shape.

It is also possible to form the bearing member 19 with an electrically conductive plastic.

DESCRIPTION OF THE REFERENCE NUMERALS

10 . . . beauty instrument, 11 . . . handle, 17 . . . ball, 20 . . . skin, x . . . centerline, y . . . axis, α . . . lateral projection angle, β . . . opening angle between balls, L . . . diameter of ball, D . . . distance between outer circumferential surfaces of balls.

The invention claimed is:

1. A beauty instrument comprising:
   a handle, wherein the handle comprises a tip having bifurcated portions extending in a Y-letter shape from the handle;
   a ball supporting shaft integral to each bifurcated portion, wherein each ball supporting shaft supports a ball, wherein each ball supporting shaft defines an independent axis, wherein each said ball freely rotates about the axis defined by the ball supporting shaft that supports that said ball, wherein each said ball is located at a distance from the other said ball, wherein the axes defined by the ball supporting shafts comprise a lateral projection angle with respect to a centerline of the handle, further wherein each ball comprises an outer surface, a proximal end, and a distal end, wherein the ball supporting shaft supports the ball at the proximal end of the ball by way of a bearing member fitted to said ball supporting shaft and fixed by a stop ring, and the outer surface at the distal end of the ball is not penetrated, further wherein each ball comprises a cap material surrounding a distal end of said bearing member, a core material surrounding said cap material and said bearing member, and a shell material defining said outer surface of said ball and surrounding said cap material and said core material.

2. The beauty instrument according to claim 1, wherein the lateral projection angle of the axis of each ball with respect to the centerline of the handle is set in a range from 90 degrees to 110 degrees.

3. The beauty instrument according to claim 2, wherein the lateral projection angle of the axis of each ball is set in a range from 93 degrees to 100 degrees.

4. The beauty instrument according to claim 3, wherein the lateral projection angle of the axis of each ball is set in a range from 95 degrees to 99 degrees.

5. The beauty instrument according to claim 1, wherein an opening angle between the balls is set in a range from 50 degrees to 110 degrees.

6. The beauty instrument according to claim 5, wherein the opening angle between the balls is set in a range from 50 degrees to 90 degrees.

7. The beauty instrument according to claim 6, wherein the opening angle between the balls is set in a range from 65 degrees to 80 degrees.

8. The beauty instrument according to claim 1, wherein a diameter of the balls is set in a range from 15 mm to 60 mm.

9. The beauty instrument according to claim 8, wherein the diameter of the balls is set in a range from 32 mm to 55 mm.

10. The beauty instrument according to claim 9, wherein the diameter of the balls is set in a range from 38 mm to 45 mm.

11. The beauty instrument according to claim 1, wherein a distance between the outer circumferential surfaces of the balls is in a range from 8 mm to 25 mm.

12. The beauty instrument according to claim 11, wherein the distance between the outer circumferential surfaces of the balls is set in a range from 9 mm to 15 mm.

13. The beauty instrument according to claim 12, wherein the distance between the outer circumferential surfaces of the balls is set in a range from 10 mm to 13 mm.

14. The beauty instrument according to claim 1, wherein a radius of curvature of a part of the outer circumferential surface of the proximal end of each ball is made greater than a radius of curvature on a part of the distal end of each ball.

* * * * *